US007419574B2

(12) United States Patent
Cummings et al.

(10) Patent No.: US 7,419,574 B2
(45) Date of Patent: *Sep. 2, 2008

(54) DIELECTROPHORESIS DEVICE AND METHOD HAVING NON-UNIFORM ARRAYS FOR MANIPULATING PARTICLES

(76) Inventors: Eric B. Cummings, 1159 Rebecca Dr., Livermore, CA (US) 94550; Yolanda Fintschenko, 819 Marceila St., Livermore, CA (US) 94550; Blake Simmons, 432 Bartlett St., San Francisco, CA (US) 94110

(*) Notice: Subject to any disclaimer, the term of this patent is extended or adjusted under 35 U.S.C. 154(b) by 626 days.

This patent is subject to a terminal disclaimer.

(21) Appl. No.: 10/760,139

(22) Filed: Jan. 16, 2004

(65) Prior Publication Data

US 2004/0211669 A1    Oct. 28, 2004

Related U.S. Application Data

(63) Continuation-in-part of application No. 10/176,322, filed on Jun. 20, 2002, which is a continuation-in-part of application No. 09/886,165, filed on Jun. 20, 2001, now Pat. No. 7,014,747.

(51) Int. Cl.
   *B01D 57/02*   (2006.01)
(52) U.S. Cl. .............. 204/547; 204/643; 204/450; 204/600; 209/127.1
(58) Field of Classification Search ............. 204/547, 204/643, 450, 600; 209/127.1
   See application file for complete search history.

(56) References Cited

U.S. PATENT DOCUMENTS

| 5,427,663 | A | * | 6/1995 | Austin et al. ............... 204/549 |
| 5,454,472 | A | * | 10/1995 | Benecke et al. ............ 209/127.1 |
| 5,858,192 | A | | 1/1999 | Becker et al. |
| 6,071,394 | A | | 6/2000 | Cheng et al. |
| 6,264,815 | B1 | | 7/2001 | Pethig et al. |
| 6,310,309 | B1 | | 10/2001 | Ager et al. |
| 6,368,871 | B1 | * | 4/2002 | Christel et al. ............. 436/180 |
| 6,596,143 | B1 | | 7/2003 | Wang et al. |
| 6,641,708 | B1 | * | 11/2003 | Becker et al. .............. 204/547 |
| 6,685,810 | B2 | * | 2/2004 | Noca et al. ................. 204/450 |
| 6,685,841 | B2 | * | 2/2004 | Lopez et al. ............... 210/767 |
| 6,749,736 | B1 | | 6/2004 | Fuhr et al. ................. 204/643 |
| 6,824,664 | B1 | * | 11/2004 | Austin et al. ............... 204/643 |
| 6,875,329 | B2 | | 4/2005 | Washizu et al. ............ 204/547 |
| 6,881,315 | B2 | | 4/2005 | Iida et al. .................. 204/600 |
| 7,014,747 | B2 | * | 3/2006 | Cummings et al. ......... 204/643 |
| 7,204,923 | B2 | * | 4/2007 | Cummings ................. 204/547 |

(Continued)

OTHER PUBLICATIONS

Fiechtner et al., "Faceted Design of Channels for Low-Dispersion Electrokinetic Flows in Microfluidic Systems", Analytical Chemistry, 2003, 75(18):4747-4755.

(Continued)

*Primary Examiner*—Nam Nguyen
*Assistant Examiner*—Surekha Vathyam

(57) ABSTRACT

Microfluidic devices according to embodiments of the present invention include an inlet port, an outlet port, and a channel or chamber having a non-uniform array of insulating features on one or more surfaces. Electrodes are provided for generation of a spatially non-uniform electric field across the array. A voltage source, which may be an A.C. and/or a D.C. voltage source may be coupled to the electrodes for the generation of the electric field.

1 Claim, 4 Drawing Sheets

U.S. PATENT DOCUMENTS

| | | |
|---|---|---|
| 2002/0175079 A1 | 11/2002 | Christel et al. |
| 2003/0010637 A1 | 1/2003 | Cummings |
| 2004/0026250 A1 | 2/2004 | Cummings et al. |
| 2004/0226819 A1* | 11/2004 | Talary et al. ................. 204/451 |
| 2005/0072676 A1 | 4/2005 | Cummings et al. ........... 204/547 |

OTHER PUBLICATIONS

Huang et al., "Introducing Dielectrophoresis as a New Force Field for Field-Flow Fractionation", Biophysical Journal, Aug. 1997, 73:1118-1129.

Pohl, "The Motion and Precipitation of Suspensoids in Divergent Electric Fields", Journal of Applied Physics, Jul. 1951, 22(7):869-871.

Yang et al, "Cell Separation on Microfabricated Electrodes Using Dielectrophoretic/Gravitational Field-Flow Fractionation", Anal. Chem., 1999, 71:911-918.

J.I. Molho et. al., "Fluid Transport Mechanisms in Microfluidic Device," Micro-Electro-Mechanical Systems (MEMS), *1998 ASME International Mechanical Engineering Congress and Exposition* (DSC-vol. 66), 8 pages total (available at http://mems.standford.edu/~aeh/publications/Molho_asme98.pdf.

* cited by examiner

DIELECTROPHORESIS DEVICE AND METHOD HAVING NON-UNIFORM ARRAYS FOR MANIPULATING PARTICLES

CROSS-REFERENCE TO RELATED APPLICATIONS

This application is a continuation-in-part of U.S. application Ser. No. 10/176,322, filed Jun. 20, 2002 which is a continuation-in-part of U.S. application Ser. No. 09/886,165, filed on Jun. 20, 2001, both of which applications are incorporated herein by reference.

STATEMENT REGARDING FEDERALLY-FUNDED RESEARCH

This invention was made with Government support under government contract no. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

TECHNICAL FIELD

The present invention relates to manipulation of particles, and more particularly, to dielectrophoresis.

BACKGROUND OF THE INVENTION

Dielectrophoresis (DEP) is the motion of particles caused by the effects of conduction and dielectric polarization in non-uniform electric fields. Unlike electrophoresis, where the force acting on a particle is determined by its net charge, the dielectrophoresis force depends on the geometrical, conductive, and dielectric properties of the particle. A complex conductivity of a medium can be defined as $\sigma^* = \sigma + i\omega\epsilon$, where $\sigma$ is the real conductivity and $\epsilon$ is the permittivity of the medium, i is the square root of $-1$, and $\omega$ is the angular frequency of the applied electric field, E. According to well-known theory, the dielectrophoretic force is proportional to the differences in complex conductivity of the particle and suspending liquid and square of the applied electric field. Without being bound by theory, for a spherical particle of radius r, the DEP force, $F_{DEP}$ is given by $$F_{DEP} = 2\pi r^3 \epsilon_m Re[f_{CM}] \nabla E^2$$

where $\epsilon_m$ is the absolute permittivity of the suspending medium, E is the local (rms) electric field, $\nabla$ is the del vector operator and $Re[f_{CM}]$ is the real part of the Clausius-Mossotti factor, defined as:

$$f_{CM} = \frac{\sigma_p^* - \sigma_m^*}{\sigma_p^* + 2\sigma_m^*}$$

where $\sigma_p^*$ and $\sigma_m^*$ are the complex conductivities of the particle and medium respectively, as described in M. P. Hughes, et. al. *Biochimica et Biophysica Acta* 1425 (1998) 119-126, incorporated herein by reference. Depending on the conductivities of the particle and medium, then, the dielectrophoresis force may be positive (positive DEP), or negative (negative DEP).

Thus, when a dielectric particle is exposed to an electric field, it conducts and polarizes. The size and direction of the induced electric current and dipole depend on the frequency of the applied field and electrical properties of the particle and medium, such as conductivity, permittivity, morphology and shape of the particle. Typically in an inhomogeneous field, this causes a force due to the interaction of the induced dipole and the electric field. Particles may also be moved in electric fields due to a gradient in the field phase (typically exploited in electrorotation and traveling wave dielectrophoresis), see for example Pohl H. A., *J. Appl. Phys.*, 22, 869-871; Pohl, H. A., *Dielectrophoresis*, Cambridge University Press; Huang Y., R. C. Gascoyne et al., *Biophysical Journal*, 73, 1118-1129; Wang X. B., Gascoyne, R. C., *Anal. Chem.* 71, 911-918, 1999; and U.S. Pat. No. 5,858,192, all of which are hereby incorporated by reference.

Typical devices and methods employing dielectrophoresis to manipulate particles employ electrodes shaped or arranged to generate a spatially non-uniform electric field, and therefore dielectrophoretic forces. Particles are generally drawn toward the electrode edges, or toward electric field minimums between electrode regions. This limits the particles to be manipulated to those that are compatible with the electrodes, electrode materials, electrochemical products, and sharp electric field gradients in the immediate vicinity of the electrodes.

SUMMARY OF THE INVENTION

According to an aspect of the present invention, a device for manipulating particles using dielectrophoresis is provided. A non-uniform array of insulating features is formed on a substrate. A plurality of electrodes is positioned to generate a spatially non-uniform electric field across the non-uniform array.

According to another aspect of the present invention, a method for manipulating particles using dielectrophoresis is provided. A spatially non-uniform electric field is generated across a non-uniform array of insulating features. A sample fluid containing the particles is passed across the non-uniform array. The spatially non-uniform electric field exerts a dielectrophoresis force on the particles thereby constraining motion of at least one particle. At least one particle is trapped at a location in the non-uniform array, where the location is determined at least in part based on electric and geometrical properties of the particle.

DETAILED DESCRIPTION OF PREFERRED EMBODIMENTS

Embodiments of the present invention provide methods and devices for manipulating particles using dielectrophoresis. The manipulations may include but are not limited to, concentrating, transporting, filtering, capturing (trapping), and/or dispersing, as described further below.

Microfluidic devices according to embodiments of the present invention include an inlet port, an outlet port, and a channel or chamber having a non-uniform array of insulating features on one or more surfaces. Electrodes are provided for generation of a spatially non-uniform electric field across the array. A voltage source, which may be an A.C. and/or a D.C. voltage source may be coupled to the electrodes for the generation of the electric field.

Figure 1:
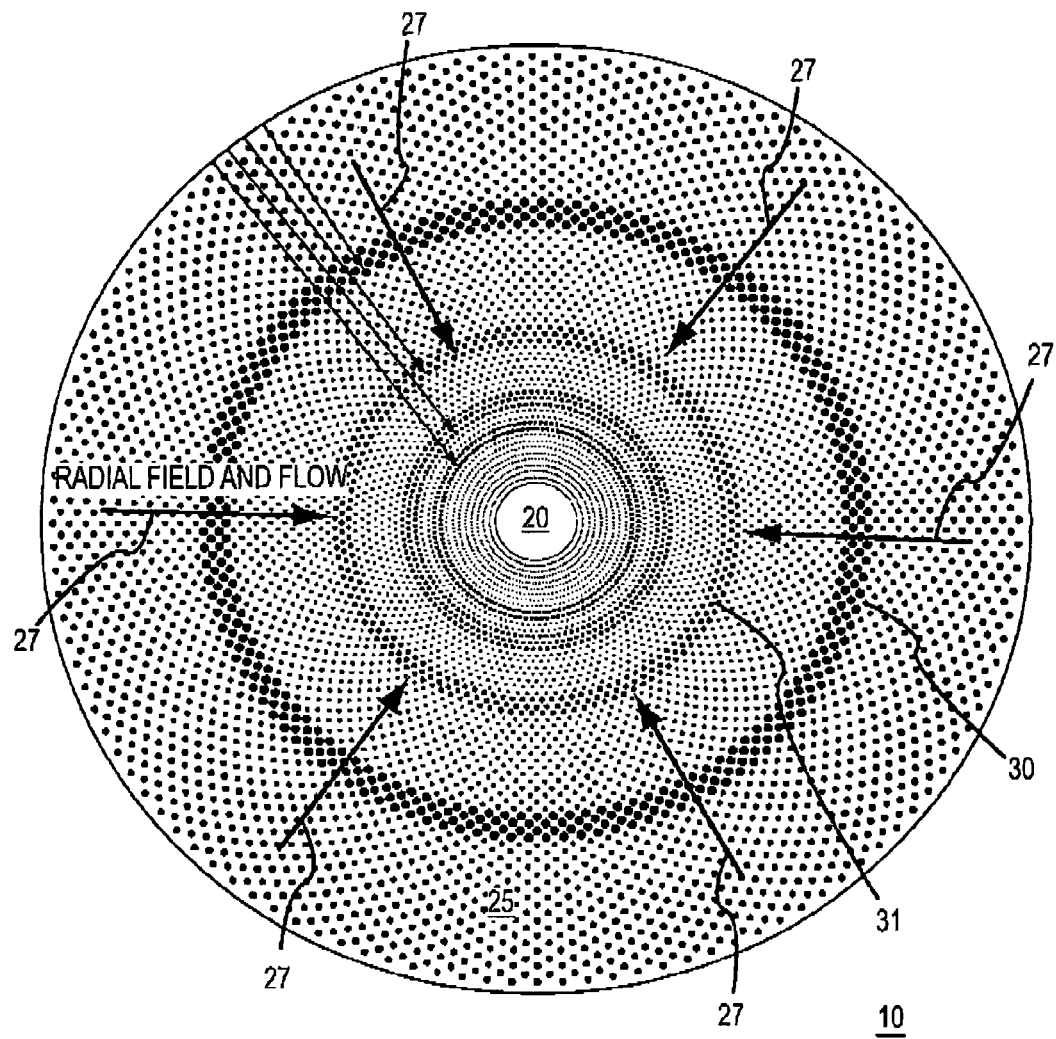
FIG. 1 is a top plan view of a microfluidic device according to one example of the invention.
Figure 2:
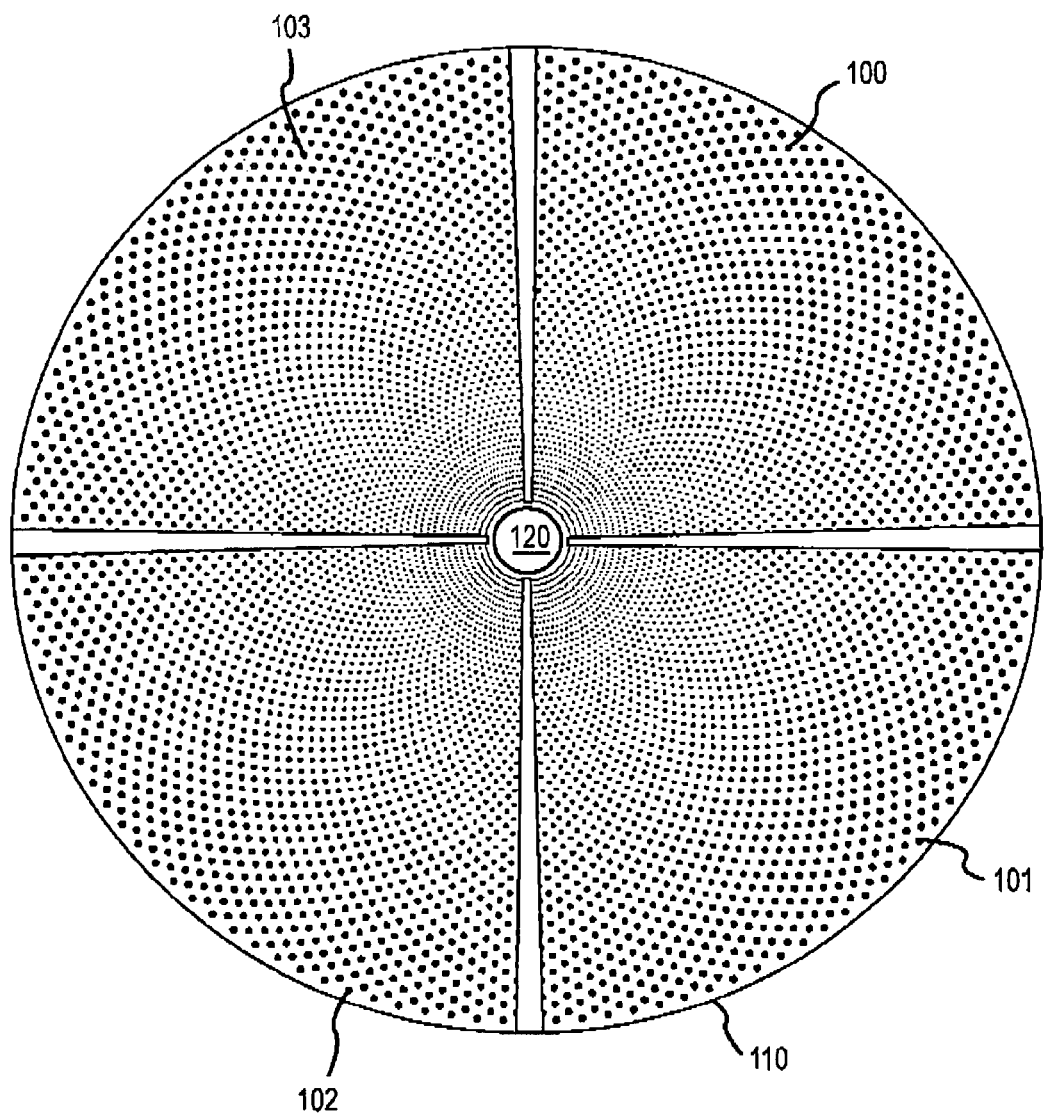
FIG. 2 is a top plan view of a microfluidic device according to one example of the invention.

One example of a device according to an embodiment of the present invention is shown in FIG. 1. A non-uniform array 25 of insulating features is positioned in a dielectrophoresis chamber 10. Although shown as posts in FIG. 1, the insulating features in other embodiments are implemented as rods, dips, dimples, valleys, ridges, or other structures and combinations thereof. In some embodiments, the insulating features span all or most of the chamber or channel depth, such as posts. In other embodiments, the insulating features are implemented on one or more surfaces of the chamber or channel, and may be stamped or embossed on one or more surfaces, for example. In embodiments where the insulating features are stamped or embossed on one or more surfaces of the channel, radial walls, posts, medians, or other features may be provided spanning the depth of the channel or chamber in order to support a cover. The non-uniform array 25 includes a plurality of features that change in size and/or shape along a direction of particle motion in the dielectrophoresis chamber 10. Generally, by "non-uniform array" of insulating features, herein is meant a plurality of insulating features, where the size, shape, and/or spacing between at least two of the features is different relative to one another. In some embodiments, the insulating features vary gradually in size across a region of a chamber or a length of a channel. In the illustrated embodiment of FIG. 1, the features are posts varying in radius proportional to their distance from the center of the dielectrophoresis chamber 10. In other embodiments, the size or shape of the insulating features changes discretely over an area of a chamber or length of a channel. In some embodiments, the spacing between array angle gradually changes with respect to the flow direction. In some embodiments, the channel boundaries change gradually or abruptly. In other embodiments, a combination of these variations is used. Generally, gradual variations refer to those over the course of multiple features, each feature bearing part of the change. An abrupt or discrete change is a change over the course of one or a small number of features. The variation in size and/or shape of the insulating features in the non-uniform array is designed to exert a non-uniform dielectrophoresis force on particles traversing the array, such that particles having different dielectrophoretic mobilities may be segregated, as described further below.

In embodiments of the present invention, particles are manipulated in the dielectrophoresis chamber by exerting both a dielectrophoresis force and a "mobilization force" on the particle. Applying an electric field 27 across the array 25 generates a dielectrophoresis force. The insulating features generate a spatially non-uniform electric field within the array 25, thereby generating a dielectrophoresis force on a particle. The mobilization force may be, for example, an electrokinetic force, a pressure force, an inertial force, a gravitational force, a magnetic force, or a combination of these andlor other forces. That is, particles may be mobilized by electrokinesis, advection, sedimentation, buoyancy, magnetophoresis, other hydrodynamic forces, and/or the like. In the embodiment shown in FIG. 1, when an electric field having a non-zero D.C. component is applied between an outer and inner electrode, the particles experience an electrokinetic force in the direction of the electric field 27. Based on the electrokinetic mobility and the complex conductivity and size of the particles, the competition between the electrokinetic force and the dielectrophoresis force causes the particles to be trapped in a radial ring 30.

During operation, an electric field 27 is applied across the non-uniform array 25. In the example shown in FIG. 1, the electric field 27 is applied between an outer radial electrode and an inner electrode (not shown). The electric field may have any general wave form—including sine and square waveforms, for example. In embodiments where electrokinesis is all or part of the manipulation force, the applied electric field has a near zero-frequency, or D.C., component. The particular electric field strengths used depend on the particles to be manipulated, the applied field frequency components, and the particle-bearing fluid. For example, in some embodiments where anthrax or *E. coli* are manipulated in de-ionized water, a zero-frequency (direct-current or DC) field strength of a few hundred Volts to a few thousand Volts across 12.5 mm immobilizes the particles against electrokinetic flow on features having a characteristic dimension of ~100 μm.

The non-uniform array 25 of insulating features generates a spatially non-uniform electric field within the dielectrophoresis chamber 10. A particle will experience a varying dielectrophoresis force as the particle traverses the non-uniform array 25. The non-uniform array 25 shown in FIG. 1 contains insulating features whose diameter varies as a function of their radial distance from a center of the dielectrophoresis chamber 10. Particles are immobilized, or "trapped" in a radial location, such as a ring 30, based on their dielectrophoretic mobility. As the particles progress toward the center, they experience progressively deeper dielectrophoretic potential wells because of the inverse scaling of the electric field and the inverse scaling of the spatial gradients. The position, or radius, at which particles are immobilized depends on the particle electrical and geometrical properties and the magnitudes of the applied fields. Particles having larger absolute dielectrophoretic mobility are trapped at larger radii. Particles having a larger absolute electrokinetic mobility are trapped at smaller radii. This trapping is stable, in that if a particle escapes from a trap, it propagates inward to a region where the fields are stronger, trapping the particle. The non-uniform array 25 shown in FIG. 1 can also be described as an array of insulating features whose size and spacing varies proportionally to their distance from a "vanishing point", where, in the embodiment of FIG. 1, the "vanishing point" is the outlet 20.

By lowering the applied electric fields over time, particles can be moved toward the outlet 20 in the center of the array 25. Accordingly, for example, by lowering the applied field, particles immobilized in the annular ring 30 are moved to annular ring 31. To move particles outward, such as from the annular ring 31 to the annular ring 30, the mobilization field polarity is reversed and the magnitude of the electric field lowered. This releases the particles and transports them radially outward. The electric field is then increased to retrap the particles at a larger radius. If this retrapping is performed with the mobilization field reversed (driving the particles outward) the system is unstable, in that if a particle misses its trap, it will encounter progressively weaker traps as it progresses outward. Therefore, the particles are generally driven outward for a time, and then the mobilization field is again reversed to drive the particles inward and the magnitude of the applied electric field is increased to retrap the particles. This can be repeated in a sequence, for example, to elute particles out of either the inlet or outlet port.

The embodiment shown in FIG. 2 shows a four-quadrant radial non-uniform array. Quadrants 100, 101, 102, and 103 share an annular input port 110 and a circular exit port 120. Each of the quadrants 100, 101, 102, and 103 contains a different non-uniform array of insulating features. Any number of arc 'slices', such as the quadrants 100, 101, 102, and 103, may be included in a device according to embodiments of the present invention.

Figure 3:
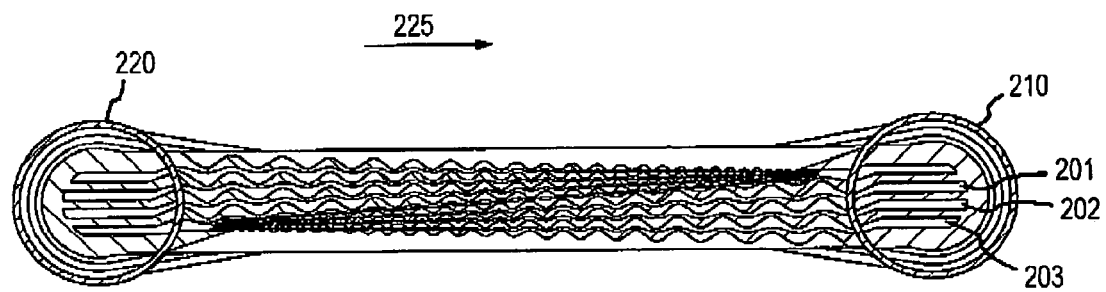
FIG. 3 is a top plan view of a microfluidic device according to another example of the invention.

FIG. 3 depicts an embodiment of a device according to the present invention having a plurality of channels, including channels 201, 202, and 203 with a non-uniform array of features along the walls of the channels. In the example shown in FIG. 3, the non-uniform array includes waves, or protrusions, of varying width along the length of the channels 201, 202 and 203. Inlet and outlet ports 210 and 220 are provided for access to the channels 201, 202, and 203. As an electric field is applied across the device in the direction shown by arrow 225, particles are trapped at a distance along the channels 201, 202, and 203 dependent on their electrical and/or physical properties and the strength of the applied fields. In this manner, particles are separated according to their electric and/or geometrical properties in an analogous manner to separating particles in the radial embodiment shown in FIG. 1 and described above.

Accordingly, particles may be concentrated or separated during bulk fluid flow using devices and methods of the present invention. This allows, for example, embodiments where a large volume of fluid-milliliters, pints, liters, or quarts, may be passed through a device and particles within that fluid manipulated. In some embodiments, however, small volumes of fluid—microliters, nanoliters, or picoliters of fluid are manipulated. Generally, any amount of fluid may be manipulated using embodiments of the invention. For example, a quantity of water is passed through a device in one embodiment, and the bacteria or other contaminants in the water are removed.

Particles manipulated in accordance with embodiments of the invention may include biological or non-biological particles, generally ranging in size from 5 nm to 200 µm in diameter. However, smaller and larger particles may also be manipulated in some embodiments depending on the strength of the applied electric field, the magnitude of gradients of the electric field, and the conductivity and permittivity of the particle and the fluid, as described further below. Further, particles may have generally any shape. Manipulated particles include generally any particle conducting or forming a dipole differently than its displaced fluid in response to an applied electric field. In some embodiments, however, target particles are attached to other particles so as to alter their dielectrophoretic behavior, e.g., to reduce the field or field gradients needed to manipulate the target particles or to enhance specificity or effect a separation of the target particles from other particles.

Suitable particles include, but are not limited to, large chemical molecules, in some embodiments generally molecules larger than about 10 kD, although in some embodiments smaller molecules are manipulated depending on the strength of the applied electric field, geometry of the device, and composition of the carrier fluid, described further below. Suitable molecules include environmental, clinical chemicals, pollutants, toxins, and biomolecules, including, but not limited to, pesticides, insecticides, toxins (including biotoxins), therapeutic and abused drugs, hormones, antibiotics, antibodies, organic materials, etc. Suitable biomolecules include, but are not limited to, proteins (including enzymes, immunoglobulins and glycoproteins), nucleic acids, lipids, lectins, carbohydrates, hormones, whole cells (including procaryotic (such as pathogenic bacteria) and eucaryotic cells, including mammalian tumor cells), viruses, spores, amoeba, yeasts, etc.

Particles manipulated by embodiments of the present invention may further include particles sampled from air or other gaseous samples, including for example, dirt, diesel soot, dust, pollens, rubber particles, metallic particles, and metallic oxide particles, or any other particle collected from a gas sample.

In some embodiments, manipulated particles include a protein or proteins. By "proteins" or grammatical equivalents herein is meant proteins, oligopeptides and peptides, derivatives and analogs, including proteins containing non-naturally occurring amino acids and amino acid analogs, peptidomimetic structures, multiple-protein structures, enzymes, and any other particle that is now or subsequently recognized as being a protein.

In some embodiments, the manipulated particles include nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones. As will be appreciated by those in the art, all of these nucleic acid analogs may find use in the present invention. In addition, mixtures of naturally occurring nucleic acids and analogs can be made; alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

Suitable particles for manipulation include biomolecules associated with: viruses, bacteria, amoeba, enzymes, carbohydrates and lipids.

Other suitable particles include but are not limited to magnetic particles, high-magnetic-permeability particles, metal ions, metal ion complexes, inorganic ions, inorganic ion complexes, organometallic compounds and inorganic compounds, particularly heavy and/or toxic metals, including but not limited to, aluminum, arsenic, cadmium, chromium, selenium, cobalt, copper, lead, silver, nickel, or mercury.

In preferred embodiments, the manipulated particle comprises a biotoxin. As will be appreciated by those in the art, there are a large number of possible biotoxins that may be identified using embodiments of the present invention, including, but not limited to, ricin, botulinum toxin, tetanus toxin, cholera toxin, abrin, aflotoxins, and conotoxins.

In preferred embodiments, the manipulated particle comprises a weapon degradation product. Degradation products that may be identified using embodiments of the present invention include, but are not limited to, alkylphosphonic acids and related monoesters.

In preferred embodiments, the manipulated particle comprises an explosive. Explosives that may be identified using embodiments of the present invention include, but are not limited to, RDX, HMX, tetryl, trinitrotoluene, other nitrotoluenes and nitroaramines.

Particles to be manipulated in accordance with embodiments of the present invention are generally suspended in a fluid. Fluid samples containing particles and useful with embodiments of the present invention may include substantially any liquid compatible with the particle of interest. Water, including deionized water, or buffer fluids are used in some embodiments. In some embodiments, a biological fluid sample is used such as bodily fluids including blood, urine, saliva or perspiration. In some embodiments, the fluid sample is mixed with additives, such as chelating molecules, growth media, pH buffering molecules, surfactant molecules, oils, and/or solvents, to alter the physical, chemical and electrical properties of the fluid, to make the fluid more benign to living organisms, to prevent aggregation and sticking of the particles to each other and surfaces, etc. As will be appreciated by those in the art, the sample fluid may comprise any number of things, including, but not limited to, bodily fluids (including, but not limited to, blood, urine, serum, lymph, saliva, anal and vaginal secretions, perspiration and semen; and solid tissues, including liver, spleen, bone marrow, lung, muscle, brain, etc.) of virtually any organism, including mammalian samples; environmental samples (including, but not limited to, air, agricultural, water and soil samples); biological warfare agent samples; research samples (e.g., in the case of nucleic acids, the sample may be the products of an amplification reaction; or in the case of biotoxins, control samples, for instance; purified samples, such as purified genomic DNA, RNA, proteins, etc.); raw samples (bacteria, virus, genomic DNA, etc.). As will be appreciated by those in the art, virtually any experimental manipulation may have been done on the sample prior to its use in embodiments of the present invention. For example, a variety of manipulations may be performed to generate a liquid sample of sufficient quantity from a raw sample. In some embodiments, gas samples and aerosol samples are passed through a collector to generate a liquid sample containing particles present in the original sample. In this manner, environmental sampling of gas and/or aerosols may be used. In some embodiments, a liquid may be contacted with a solid sample to disperse the particles into the liquid for subsequent analysis. Other fluids of interest include, for example, carbonated beverages, juices, blood, blood serum, fresh water, salt water, sea water, petroleum, and various fermentation broths.

Microfluidic devices according to embodiments of the present invention generally include a substrate. The substrate may be made of any of a variety of substantially low-conductivity materials or materials that are bounded by a low-conductivity coating in the region of the ridges. However, in some embodiments, other materials may be used. Suitable substrate materials include, but are not limited to, silicon, silicon dioxide, alumina, boron nitride, silicon nitride, diamond glass and fused silica, gallium arsenide, germanium, indium phosphide, III-V materials, PDMS, SU-8, silicone rubber, aluminum, ceramics, polyimide, quartz, plastics, resins and polymers including polymethylmethacrylate, acrylics, polyethylene, polyethylene terepthalate, polycarbonate, polystyrene and other styrene copolymers, polypropylene, polytetrafluoroethylene, superalloys, zircaloy, steel, gold, silver, copper, tungsten, molybdeumn, tantalum, SU-8, ZEONOR, TOPAZ, KOVAR, KEVLAR, KAPTON, MYLAR, teflon, etc. High quality glasses such as high melting borosilicate or fused silicas may be preferred for their UV transmission properties. Fired ceramics, either naturally occurring or synthetic, may be preferred for their comparatively low cost. Insulating materials or coatings are preferred for the substrate. In the case where conducting materials are used for the substrate, the conducting materials are preferably coated with an insulating material.

In some embodiments one or more of the insulating features in a non-uniform array are made from the same material as the substrate. In some embodiments, however, the feature is made of a different material deposited or adhered to the substrate. The feature may generally be formed of any of the above-listed materials or of some other material. In preferred embodiments, the feature is an insulating feature, made entirely from insulating materials or simply coated with an insulating material. Embodiments of features useful in the present invention have heights that span a small fraction (e.g., 0.001%) of the height of the fluid on the substrate, in which case the induced field concentration is localized near the surface, to a large fraction (e.g., 99.999%) of the height of the liquid in the channel, in which case the electric field concentration is extreme and less localized to obstacles that span the entire height (100%) of the channel, including obstacles that form channel walls. The typical useful range is more moderate, e.g., 10%-to-90% or 100% for ease in fabrication, prevention of unwanted dispersion and dead volume.

From the foregoing it will be appreciated that, although specific embodiments of the invention have been described herein for purposes of illustration, various modifications may be made without deviating from the spirit and scope of the invention. Accordingly, the invention is not limited except as by the appended claims.

EXAMPLE

FIGS. 4a-d are photographs of a time sequence of ploystyrene particle collection and release in a wavy-wall based non-uniform array, such as that depicted in FIG. 3. The wavelength of the sinusoidal wall in this region is approximately 500 µm. The time-sequence photographs shown in FIG. 4 are an example of a use of a wavy-wall design for particle sorting and collection.

The light regions are from fluorescence of mixture of 1 µm and 200-nm particles. The liquid and electrokinetic particle flow is from bottom to top driven by an applied electric field of about 50 V/mm (initial condition) in FIG. 4a, after applying 250 V/mm for 3 s in FIG. 4b, about 200 V/mm (immediately after reducing the field) in FIG. 4c, and about 200 V/mm after 3s, shown in FIG. 4d. At the conditions of the experiments the particles are less conductive than the solution and exhibit negative dielectrophoresis.

Figure 4A:
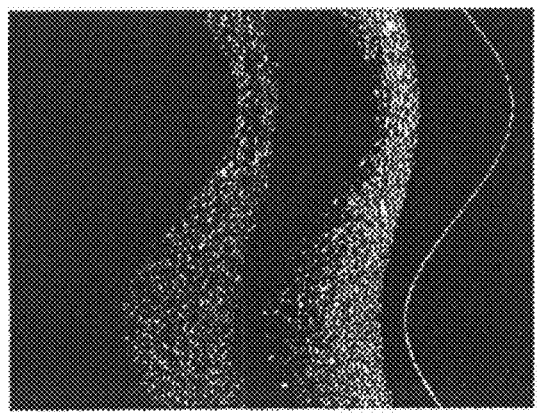
FIGS. 4a-d are photographs of an example of the invention during operation.
Figure 4B:
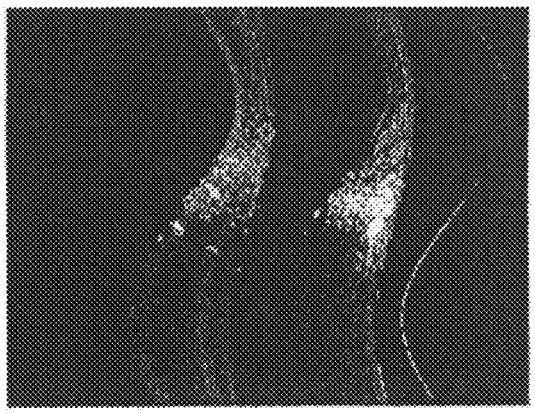
Figure 4C:
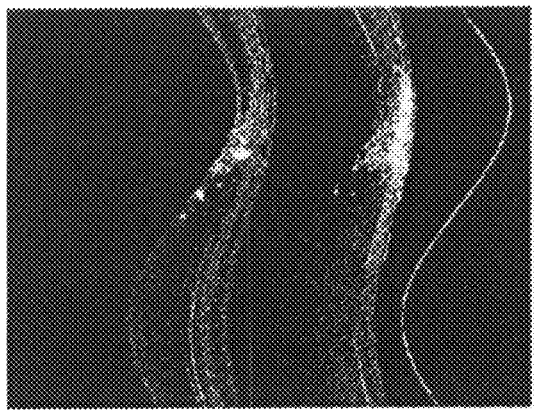
Figure 4D:
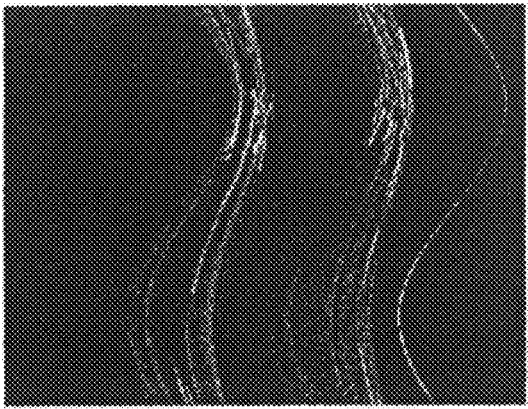

Applying the field of about 250 V/mm traps the 1-µm particles while passing the 200 nm particles (see FIG. 4b). Reducing the field releases the 1-µm particles to trap at a downstream site (see FIGS. 4c and 4d). For visual clarity, a large number of particles are used, consequently the traps are saturated or nearly saturated.

What is claimed is:

1. A method for manipulating particles using dielectrophoresis, the method comprising:
    passing a sample fluid containing the particles across a non-uniform radial array of insulating features;
    generating a spatially non-uniform electric field, the spatially non-uniform electric field exerting a dielectrophoretic force on the particles thereby constraining motion of at least one particle;
    trapping at least one particle at a location in the non-uniform array, wherein the location is determined at least in part based on electric and geometrical properties of the particle; and
    trapping the particles in a ring around a center of the radial array.

* * * * *